United States Patent
Freiburger et al.

(10) Patent No.: US 10,004,474 B2
(45) Date of Patent: Jun. 26, 2018

(54) TISSUE DENSITY QUANTIFICATION USING SHEAR WAVE INFORMATION IN MEDICAL ULTRASOUND SCANNING

(75) Inventors: Paul Freiburger, Seattle, WA (US); Liexiang Fan, Sammamish, WA (US); Roee Lazebnik, San Jose, CA (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 877 days.

(21) Appl. No.: 12/913,599

(22) Filed: Oct. 27, 2010

(65) Prior Publication Data

US 2012/0108968 A1    May 3, 2012

(51) Int. Cl.
*A61B 8/08*    (2006.01)
*G01S 7/52*    (2006.01)

(52) U.S. Cl.
CPC ............ *A61B 8/0825* (2013.01); *A61B 8/485* (2013.01); *A61B 8/5223* (2013.01); *G01S 7/52042* (2013.01)

(58) Field of Classification Search
CPC ......... A61B 8/485; A61B 8/0825; A61B 5/05; A61B 5/0507; A61B 5/0536; A61B 5/4312; A61B 5/7257; A61B 6/037; A61B 6/508; A61B 8/00; A61B 8/06; A61B 8/08; A61B 8/0858; A61B 8/13; A61B 8/406; A61B 8/463; A61B 8/5223; A61B 8/5238; G06T 7/0012; G06T 2207/30004; G06T 2207/30068; G06T 7/001; G06T 7/0038
See application file for complete search history.

(56) References Cited

U.S. PATENT DOCUMENTS

| | | | |
|---|---|---|---|
| 5,107,837 A | 4/1992 | Ophir et al. | |
| 5,178,147 A | 1/1993 | Ophir et al. | |
| 5,293,870 A | 3/1994 | Ophir et al. | |
| 5,564,423 A | 10/1996 | Mele et al. | |
| 6,508,768 B1 | 1/2003 | Hall et al. | |
| 6,558,324 B1 | 5/2003 | Von Behren et al. | |
| 9,351,977 B2 * | 5/2016 | Birrell | A61K 31/4196 |
| 2003/0165262 A1 * | 9/2003 | Nishikawa | G06T 7/0012 382/128 |
| 2005/0252295 A1 * | 11/2005 | Fink | A61B 8/08 73/603 |
| 2005/0277835 A1 * | 12/2005 | Angelsen | A61B 8/14 600/437 |

(Continued)

OTHER PUBLICATIONS

Sarvazyan, A.P. et al, Shear wave elasticity imaging: A new ultrasonic technology of medical diagnostics, Ultrasound in Med. & Biol., vol. 24, No. 9, pp. 1419-1435;1998.*

(Continued)

*Primary Examiner* — Amanda Lauritzen Moher

(57) ABSTRACT

Tissue density is quantified using shear wave information in medical ultrasound scanning. Measurements of the tissue reaction to shear waves indicate tissue density. For example, shear wave velocity is linked with density using clinical study information. The shear wave velocity in a region, over the entire tissue, or at various locations is used to determine a corresponding density or densities. The tissue density information is used for categorization, estimation of disease risk, imaging, diagnosis, or other uses. The tissue may be breast tissue or other tissue.

9 Claims, 1 Drawing Sheet

(56) References Cited

U.S. PATENT DOCUMENTS

| | | | | |
|---|---|---|---|---|
| 2006/0084859 A1* | 4/2006 | Johnson | ............... | A61B 5/0507 |
| | | | | 600/407 |
| 2007/0003117 A1* | 1/2007 | Wheeler | ................ | G06T 7/001 |
| | | | | 382/128 |
| 2007/0078341 A1 | 4/2007 | Ghosh et al. | | |
| 2008/0275344 A1 | 11/2008 | Glide-Hurst et al. | | |
| 2016/0235379 A1* | 8/2016 | Homann | ................ | A61B 6/502 |

OTHER PUBLICATIONS

Heine et al. "Cumulative Sum Quality Control for Calibrated Breast Density Measurements." Med Phys. Dec. 26, 2009(12):5380-5390.*

Karen Ravn, "Breast density linked to cancer risk", latimes.com, http://www.latimes.com/news/health/la-he-breast-density-20100621.0.3428626.story, printed Sep. 21, 2010, pp. 1-3, dated Jun. 21, 2010.

Marla R. Hersh, "Imaging the dense breast", Applied Radiology, vol. 33, No. 1, Jan. 2004, printed Oct. 7, 2010.

* cited by examiner

TISSUE DENSITY QUANTIFICATION USING SHEAR WAVE INFORMATION IN MEDICAL ULTRASOUND SCANNING

BACKGROUND

The present embodiments relate to tissue density quantification. Breast density may be an indicator for breast cancer risk. Changes in breast density over time may indicate increased risk.

Breast density may be characterized using different approaches. The American College of Radiology (ACR) defines four density patterns in the Breast Imaging Reporting And Data System (BIRADS). Wolfe Patterns may be used. These patterns characterize the breast density, but there is a wide variability in radiologists' ability to categorize breast density using the Wolfe Patterns. Computer programs may use mammography imaging to attempt to categorize breast density. However, there is not currently a cheap, reliable breast density screening device available.

BRIEF SUMMARY

By way of introduction, the preferred embodiments described below include methods, instructions, and systems for quantifying tissue density using shear wave information in medical ultrasound scanning. Measurements of the tissue reaction to shear waves indicate tissue density. For example, shear wave velocity is linked with density using clinical study information. The shear wave velocity in a region, over the entire tissue, or at various locations is used to determine a corresponding density or densities. The tissue density information is used for categorization, estimation of disease risk, imaging, diagnosis, or other uses. The tissue may be breast tissue or other tissue.

In a first aspect, a method is provided for quantifying tissue density using shear wave information in medical ultrasound scanning. A shear wave is generated in a patient's breast. Acoustic energy is transmitted into the breast while the shear wave propagates within the breast. Echoes responsive to the transmitting are received while the shear wave propagates within the breast. A shear wave propagation property is estimated for each of a plurality of locations within the breast as a function of the echoes. A density of the breast is determined at each of the locations as an inverse function of the respective shear wave propagation property. An image of the density for at least one of the locations is output.

In a second aspect, a non-transitory computer readable storage medium has stored therein data representing instructions executable by a programmed processor for quantifying tissue density using shear wave information in medical ultrasound scanning. The storage medium includes instructions for measuring a property of interaction of a shear wave with tissue using ultrasound, and calculating a density of the tissue as a function of the property.

In a third aspect, a system for quantifying tissue density using shear wave information is provided. A transducer is operable to generate receive signals from received ultrasound energy. A receive beamformer is operable to output data representing tissue. A processor is configured to determine density of the tissue as a function of shear wave information represented by the data. A display is operable to display an image, the image being a function of the density.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Shear wave propagation properties indicate tissue density. A device that measures shear wave propagation properties like shear wave velocity, shear wave attenuation, shear wave dispersion and/or tissue viscosity may be used to calculate breast density or the density of other tissue. Shear wave information may be easily acquired non-invasively, reliably, and with little incremental expense using ultrasound. Ultrasound breast imaging systems or other ultrasound systems may be used to determine tissue density. The breast density determination could be used in conjunction with mammograms to better understand a woman's breast cancer risk. The density information may be used in conjunction with medication to measure the medicine's effectiveness in reducing breast density. Other uses are possible.

Figure 1:
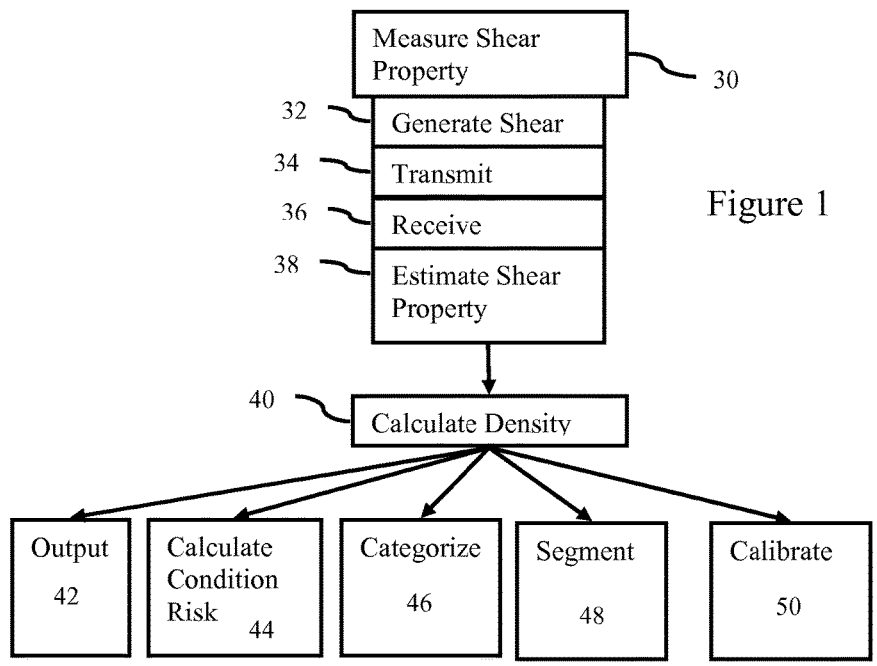
FIG. 1 is a flow chart diagram of one embodiment of a method for quantifying tissue density using shear wave information in medical ultrasound scanning.

FIG. 1 shows a method for quantifying tissue density using shear wave information in medical ultrasound scanning. The method is implemented by the system of FIG. 2 or a different system. Additional, different, or fewer acts may be provided. For example, any one, more or all of acts 42-50 are not provided. As another example, act 32 may not be actively performed, such as where heart motion is used to generate the shear. The acts are performed in the order described or shown, but may be performed in other orders.

In act 30, a property of interaction of a shear wave with tissue is measured. The measurement is made using ultrasound. Any now known or later developed shear wave measurement may be used, such as measuring shear wave velocity using the Virtual Touch™ Tissue Quantification program from Siemens Medical Solutions USA, Inc. The shear wave propagates through tissue. Various characteristics of the tissue affect the propagation, such as the velocity, dispersion, attenuation, or other propagation property of the shear wave.

The property is measured by generating the shear wave in act 32, transmitting in act 34, receiving in act 36, and estimating the property in act 38. Additional, different, or few acts may be provided. Acts 34 and 36 may be repeated in order to estimate the property in act 38. Acts 32, 34, and 36 may be repeated in order to estimate the property in act 38, such as where multiple measurements responsive to sequential shear waves are used. Acts 32, 34, 36, and 38 may be repeated in order obtain estimates of the property at different locations or times.

In act 32, a shear wave is generated in a tissue of interest. For example, the shear wave is generated in a patient's breast. Any stress may be applied to the tissue to generate the shear wave, such as generating the shear wave with focused ultrasound. For example, acoustic radiation force impulse is transmitted with a focal point at or adjacent to the tissue of interest. A high intensity (e.g., 1.7 MI) beam of acoustic energy is transmitted. Other sources of stress may be used, such as manually or internally generated stress. For example, a user applies pressure axially with a transducer. In response to the stress, a shear wave is generated.

Compression force, rarefaction force, or other stress is applied to tissue being scanned. The stress may be applied by an external source. External pressure includes acoustic or mechanical pressure. The pressure propagates from outside the patient, such as from a transducer probe, to the tissue or region of interest. The pressure may be generated from within a patient, such as acoustic pressure generated from an intra cavity probe. Acoustic pressure may be a focused or unfocused acoustic radiation force. Mechanical pressure may include a machine (e.g., thumper or vibrator).

The applied stress may be impulse, cyclical, repeating, or a non-impulse stress. For example, the pressure applied due to the heart is cyclical. The stress is applied repetitively, or differently as a function of time. The applied stress may be represented by an impulse. A substantially single pressure wave is generated. The impulse may be generated by a cyclical pulsed waveform of any number of cycles (e.g., tens or hundreds of cycles). For example, acoustic radiation force is transmitted as an impulse for applying stress to tissue. The impulse wavefront propagates to the region of interest.

In act 34, acoustic energy is transmitted in order to measure the reaction of the tissue to the shear wave. For example, acoustic energy is transmitted into the breast while the shear wave propagates within the breast.

The acoustic energy is transmitted to a plurality of locations around or at the tissue subjected to the shear wave. The tissue is scanned with ultrasound. Doppler or B-mode scanning may be used. In one embodiment, the shear wave perpendicular to the direction of the applied stress is detected by obtaining multiple B-mode scans of a small region (e.g., 4 mm in lateral and 5 mm in axial). By correlating the data from the different B-mode scans, the amplitude, velocity, or other characteristic of the shear wave is measured.

In act 36, echoes are received in response to the transmitting. While the shear wave propagates through the tissue, echoes are received from various locations for measuring the shear wave. Using the same or different transducer used to generate the shear wave, ultrasound scanning is used to measure the shear property.

The strain or displacement is measured. Ultrasound imaging is performed before, during and/or after the stress is applied. Ultrasound data is received in response to transmissions of ultrasound. The transmitting and receiving of acts 34 and 26 are performed repetitively at locations spaced from a focal point of the focused ultrasound or other origin of the shear wave.

The transmissions and receptions are performed for a single spatial location (e.g., the focal point of the applied stress), along a line, over an area, or over a volume. A sequence of transmissions and receptions are provided for each spatial location. The sequence allows determination of the displacement of the tissue as a function of time caused by the shear wave.

In act 38, a shear wave propagation property is estimated. The estimation is performed for each of a plurality of locations within the tissue. Alternatively, the estimation is performed for a single location or a global region. The estimation is a function of the echoes.

The estimation is a measurement, output of a model, or other approach for determining shear wave property. In one embodiment, a shear wave velocity is measured. The velocity property of the shear wave indicates characteristics of the tissue. Velocity may be estimated using spatial displacement caused by the shear wave and a time to peak displacement. The displacement of tissue is determined as a function of time. The displacement may be measured from tissue data, such as B-mode ultrasound data. Correlation, cross-correlation, minimum sum of absolute differences or other similarity measure is used to determine the displacement caused by the shear wave between scans. The displacements are determined along one, two, or three dimensions. In one embodiment, any one or more of the methods or systems disclosed in U.S. Pat. No. 5,107,837; 5,293,870; 5,178,147; 6,508,768 or 6,558,324 are used to generate elasticity frames of data or images as the strain information. Other methods of measuring strain with or without determining displacement of tissue in response to application or change in stress may be used. The displacement may be measured by determining tissue velocity and/or acceleration, such as using Doppler ultrasound imaging.

The shear velocity is obtained by determining a time from generation of the shear wave until detection of the shear wave at a different location. The time and distance to the location determine the velocity. The distance is known from the scan line spacing (i.e., the transmit beam position for generating the shear wave and the receive beam position for detecting the shear wave). The time is known from the relative time between generation and detection of the shear wave.

The temporal profile of displacement amplitude for a given location indicates detection of the shear wave. The profile is examined for a non-noise or single instance of variation. A peak in the profile, with or without temporal low pass filtering, indicates the passing of the shear wave front. Alternatively, other portions of the profile (e.g., beginning or ending of displacement relative to a noise floor) are used to determine the time.

Other techniques may be used to detect the peak or other location in the displacement profile. For example, a regression is applied. Since the shear wave velocity is linear, a robust linear regression with automated outlier detection may indicate the shear wave velocity. The ultrasound data for all of the sample points in the region of interest are plotted for distance as a function of time or by time and distance. The linear regression is applied to the plot or data, providing a line fit to the data. The slope of the line indicates the shear wave velocity.

Other approaches may be used. For example, data from different times is correlated to detect the shift in tissue caused by the shear wave. As another example, a feature is extracted from the temporal profiles. Principal component decomposition may be used. A correlation between the different temporal profiles is performed. The lag associated with the different distances for the different temporal profiles provides the velocity. Alternatively, a wavelet analysis may be performed. A wavelet transform is applied to the temporal profiles to identify a peak corresponding to the shear wave. A velocity value is identified from the travel time of the peak to each spatial location.

All the peak travel time data from the full region of interest may be used together, such as in linear regression. Only a subset of the data may be used, such as using data for one depth for feature extraction or regression. A single shear velocity is calculated. Alternatively, a plurality of shear velocities are calculated for the region of interest. The results may be averaged or otherwise combined. For example, linear regression is applied to ten or other number of subsets. Each subset includes data for different depth ranges, such as each subset including data for twenty different depths. Shear velocity is determined for each subset. The average shear velocity is used. A variance or other statistical information may be derived from the different shear velocities. Alternatively, a spatial representation of shear wave velocity variance within the region of interest may be provided.

Other shear wave properties may be estimated. Shear values are estimated, whether quantitative or qualitative. For example, a shear wave attenuation, shear wave dispersion, tissue viscosity, or combinations thereof are estimated as the shear wave propagation property. In one embodiment, the diffusion or dispersion of the shear wave is solved. A characteristic of the spatial extent of the shear wave is calculated. The rate of decay of the shear wave may indicate attenuation.

The shear wave property is estimated for breast tissue. In other embodiments, the shear wave property is estimated for liver, thyroid, brain, muscle or other tissues. The shear wave is generated and measured in the tissue of interest.

In act 40, the density of the tissue is calculated. The density is calculated from the estimated property. The shear velocity or other shear wave property indicates the density of the tissue. The shear wave propagates differently for different densities of tissue.

In one embodiment, the density is determined as an inverse function of the respective shear wave propagation property. Shear wave propagation is inversely proportional to tissue density, as represented mathematically as:

$$c_T = \sqrt{\frac{\mu}{\rho}} = \sqrt{\frac{E}{2(1+v)\rho}}$$

where $c_T$ is the shear wave velocity, $\mu$ is the shear modulus, E is the Young's modulus, $v$ is the Poisson's ratio, and $\rho$ is the density of the tissue. The Poisson's ratio is assumed to be 0.5 or other value or a known Poisson's ratio is used. The Young's modulus may be assumed or known.

As an alternative to solving the function, the shear wave velocity or other property for a given type of tissue may be linked to clinical study data. Using one or more properties for a given location, the likely density is determined based on training or study data. The study data may correlate a given property value (e.g., velocity) or values of multiple properties (e.g., velocity and attenuation) in combination to a specific, range, or approximation of density. For example, clinical studies classifying breast density or breast cancer risk based on density may show that certain shear wave properties indicate density. The estimated shear wave property is matched to clinical data, providing tissue density classification based on the property (e.g., velocity of 1.5 m/s indicates a tissue density as category I (range of values with or without numeric label) or a specific value).

In an alternative embodiment, the tissue viscosity is determined from estimates of shear wave dispersion. How the shear wave changes as it propagates, such as the rate of attenuation, change in speed, or other change, is used as a measure of dispersion. The tissue viscosity is calculated by measuring the shear wave phase at multiple shear wave frequencies and extracting the elastic and viscous properties from the real and imaginary components. The tissue viscosity is mapped to density, such as based on clinical study data, or is used to calculate the density using a function.

The density is calculated for one location. For example, the location is the entire region of interest, so the density is calculated as a global value. The region may be sampled at a plurality of locations, but the density is calculated as an average, other statistical value, or a single value based on estimates of shear wave property within the region. In one embodiment, the shear wave property is estimated as a global value and the density is calculated as a global value. Breast density may be determined globally for the whole breast.

In other embodiments, the density is calculated locally for specific regions like cysts and lesions or smaller regions. The density may be calculated separately for each scan or sampling location. The density for a given location may be independent of or a function of the densities and/or shear wave properties for other locations.

In act 42, an image of the density is output. The image represents the density for at least one location. In one embodiment, the image represents a two or three-dimensional region. The measured tissue densities are shown for a planar scan region or rendered for a three-dimensional volume (e.g., surface rendering of density or projection rendering using density). The image data (display or pixel values) are in a display format or may be scan converted into a display format.

Pixels of the image are modulated as a function of the densities at the respective locations. Color, brightness, luminance, hue, or other characteristic is modulated as a function of the density information. The image data is color or gray scale data, but may be scalar values prior to mapping with gray scale or color scale. The information may be mapped linearly or non-linearly to the display values. In one embodiment, the color values or brightness are assigned based on densities.

More than one tissue property may be displayed in a same image. For example, pixels at one location have color responsive to one component and hue responsive to another component. The display values at different spatial locations may be responsive to different components.

The image may include other data. For example, the color information may be overlaid on or combined with B-mode or other tissue image information. The tissue property component is used for an overlay of or combination with the other data. In other embodiments, the image is of a single value or graph representing density.

In act 44, a condition risk is calculated. Any condition may be used, such as cancer or disease conditions. The risk may be a likelihood of having the condition currently or in the future. The condition is calculated as a function of the density. The condition is calculated using a formula, model, machine-learned classifier, or other approach. A processor and corresponding instructions use the density information with any other information to calculate risk. For example, the cancer risk is determined based on studies of density or change in density in relation to cancer risk. The density alone or with other information may be used.

In one embodiment, the breast cancer risk is calculated as a function of the density. The determination of the density is repeated at different times. The difference in time is over days, weeks, months, or years. The change or difference in density, extent of density field, or other density characteristic may indicate cancer risk.

In other embodiments, the density is used for risk of condition in other tissues. For example, the liver, thyroid, brain, or muscle tissue is characterized relative to fibrosis, cancer, Alzheimer's, or muscular dystrophy, respectively. The density, change in density, distribution of density, or other density information may indicate a condition relative to the tissue. The shear wave propagation properties are linked to clinical studies classifying human tissue densities to tissue disease risk.

In act 46, the tissue is categorized. Any categorization scheme may be used. For example, breast density is categorized in one or more of numerous ways including BIRADS and/or Wolfe patterns. A processor receives or mines input information, such as the density and other information. The processor applies the BIRADS, Wolfe pattern, or other analysis. Tissue density as measured using shear wave information is combined with other tissue characteristics like Young's modulus, elastic modulus, elastic ratio, sound speed, reflectivity, absorption, and/or increased blood flow to better characterize tissue properties. Computer assisted diagnosis may be used to classify inputs from images, such as blood flow from Doppler ultrasound images, sound speed from ultrasound images, or absorption from mammography images.

In act 48, segmentation is performed. A lesion or other region of interest is identified as a function of the density. Densities at different locations within a region are estimated. Regions associated with higher, lower, or specific ranges of density may indicate differences in the tissue, such as a cancerous lesion.

A threshold is applied to the density information for segmentation. Locations within, above, or below the threshold are distinguished from other locations. Low pass filtering, region growing, border detection, or other processes may be applied to the density information to identify the locations to be segmented.

Other information may be used for segmenting. In addition to density, Young's modulus, elastic modulus, elastic ratio, sound speed, reflectivity, absorption and/or increased blood flow may indicate a lesion or other different region. Multiple thresholds or other combinations of data or processes are used to identify suspect locations.

The segmentation may be performed automatically. For example, a binary mask is applied to remove data not associated with the suspect region. As another example, the locations associated with the suspect region are highlighted, such as being color coded. Alternatively, manual segmentation is performed. A user traces the suspect region as a function of displayed densities and/or other image information.

In act 50, beamformation is calibrated. Sound may travel at different speeds due to different densities. The variation in density in tissue may cause aberrations in phased array beamformation. Beamformation may assume a speed of sound. Even a uniform density tissue may result in a speed different from the assumption. The density, whether uniform or varying, may be accounted for in beamformation. During transmit and/or receive operation, the delay profile is adjusted to account for the speed of sound. The delay or phasing applied to one or more elements is adjusted relative to other elements. The density information is used to adjust the delay profile, such as for performing aberration correction. The adjusted delay profiles may better focus the ultrasound energy. B-mode, color, Doppler, elasticity, or other imaging may more accurately represent the scanned region after accounting for the density.

Figure 2:
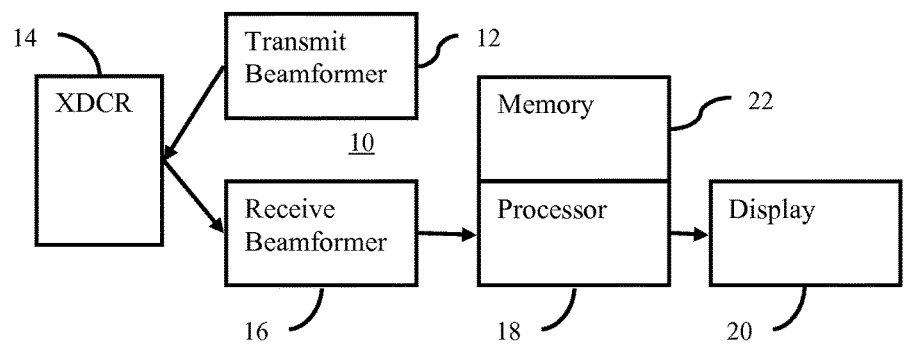
FIG. 2 is a block diagram of one embodiment of a system for quantifying tissue density using shear wave information in medical ultrasound scanning.

FIG. 2 shows one embodiment of a system 10 for quantifying tissue density using shear wave information in medical ultrasound scanning. The system 10 implements the method of FIG. 1 or other methods. The system 10 includes a transmit beamformer 12, a transducer 14, a receive beamformer 16, an image processor 18, a display 20, and a memory 22. Additional, different, or fewer components may be provided. For example, a user input is provided for manual or assisted selection of display maps, tissue properties to be determined, region of interest selection, or other control. The system 10 is a medical diagnostic ultrasound imaging system. In alternative embodiments, the system 10 is a personal computer, workstation, PACS station, or other arrangement at a same location or distributed over a network for real-time or post acquisition imaging, so may not include the beamformers 12, 16 and transducer 14.

The transmit beamformer 12 is an ultrasound transmitter, memory, pulser, analog circuit, digital circuit, or combinations thereof. The transmit beamformer 12 is operable to generate waveforms for a plurality of channels with different or relative amplitudes, delays, and/or phasing. Upon transmission of acoustic waves from the transducer 14 in response to the generated waves, one or more beams are formed. A sequence of transmit beams are generated to scan a two or three-dimensional region. Sector, Vector®, linear, or other scan formats may be used. The same region is scanned multiple times. For flow or Doppler imaging and for shear wave imaging, a sequence of scans is used. In Doppler imaging, the sequence may include multiple beams along a same scan line before scanning an adjacent scan line. For shear wave imaging, scan or frame interleaving may be used (i.e., scan the entire region before scanning again). In alternative embodiments, the transmit beamformer 12 generates a plane wave or diverging wave for more rapid scanning.

The transducer 14 is a 1-, 1.25-, 1.5-, 1.75- or 2-dimensional array of piezoelectric or capacitive membrane elements. The transducer 14 includes a plurality of elements for transducing between acoustic and electrical energies. Receive signals are generated in response to ultrasound energy (echoes) impinging on the elements of the transducer. The elements connect with channels of the transmit and receive beamformers 12, 16.

The receive beamformer 16 includes a plurality of channels with amplifiers, delays, and/or phase rotators, and one or more summers. Each channel connects with one or more transducer elements. The receive beamformer 16 applies relative delays, phases, and/or apodization to form one or more receive beams in response to each transmission. In alternative embodiments, the receive beamformer 16 is a processor for generating samples using Fourier or other transforms.

The receive beamformer 16 may include a filter, such as a filter for isolating information at a second harmonic or other frequency band relative to the transmit frequency band. Such information may more likely include desired tissue, contrast agent, and/or flow information. In another embodiment, the receive beamformer 16 includes a memory or buffer and a filter or adder. Two or more receive beams are combined to isolate information at a desired frequency band, such as a second harmonic, cubic fundamental, or other band.

The receive beamformer 16 outputs beam summed data representing spatial locations. The spatial locations are tissue or fluid regions within the patient. Data representing tissue for a single location, locations along a line, locations for an area, or locations for a volume are output. Dynamic focusing may be provided. The data may be for different purposes. For example, different scans are performed for B-mode or tissue data than for Doppler or flow data.

The processor 18 is a B-mode detector, Doppler detector, pulsed wave Doppler detector, correlation processor, Fourier transform processor, application specific integrated circuit, general processor, control processor, image processor, field programmable gate array, digital signal processor, analog circuit, digital circuit, combinations thereof or other now known or later developed device for detecting and processing information from beamformed ultrasound samples.

In one embodiment, the processor 18 includes one or more detectors and a separate processor. The processor is a control processor, general processor, digital signal processor, application specific integrated circuit, field programmable gate array, network, server, group of processors, data path, combinations thereof or other now known or later developed device for estimating shear wave properties, calculating density, generating an image, calculating condition risk, categorizing, segmenting, or calibrating. For example, the processor 18 performs any combination of one or more of the acts shown in FIG. 1.

The processor 18 determines density of the tissue as a function of shear wave information represented by the data. After causing creation of the shear wave and ultrasound scanning to measure the effects on the tissue of the shear wave, the processor 18 estimates the shear wave velocity or other property. The time to peak displacement and distance of shear wave travel may be used to determine the velocity. The processor 18 uses the shear wave property as a value of a variable in a function or as an input value to a look-up table to determine the density. Other information may be used as well. The density may be determined as an estimate or approximate value or may be calculated as a specific value.

The processor 18 performs the determination of density for one or more spatial locations. For example, a global density value representing a region of interest of tissue is determined. Any size region of interest may be used for the global value, such as a region extending over multiple beamformer sampling locations. As another example, the processor 18 determines the density at a plurality of locations in a plane or volume. The locations are the same as the beamformer sampling locations, but may be sparser.

For determining modulus or other information, the processor 18 may determine strain information (e.g., strain, displacement, or strain rate) as a function of the output data from the receive beamformer 16. The tissue property values are calculated as a function of the strain information and the moduli or tissue property. Any viscoelastic tissue property may be determined, such as the shear modulus. The processor 18 outputs image or display values mapped from the tissue properties to the display 20.

For determining density, shear wave property, strain information, modulus information, stress, or tissue properties, data from a plurality of scans or measurements may be acquired and stored. The data is stored in the memory 22 or a different memory. Data from one or more stages of processing is stored, such as radio frequency data, channel data, beam sum data, detected data, strain data, stress data, modulus data, shear modulus data, and/or calculated values.

The processor 18 operates pursuant to instructions stored in the memory 22 or another memory. The processor 18 is programmed for quantifying tissue density using shear wave information in medical ultrasound scanning. The memory 22 is a non-transitory computer readable storage media. The instructions for implementing the processes, methods and/or techniques discussed herein are provided on the computer-readable storage media or memories, such as a cache, buffer, RAM, removable media, hard drive or other computer readable storage media. Non-transitory computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing, and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

The display 20 is a CRT, LCD, projector, plasma, or other display for displaying two-dimensional images or three-dimensional representations. The display 20 displays ultrasound images, density values, shear wave property values, or other information for one or a plurality of spatial locations. For example, the image represents the density at different locations using color, brightness, or gray scale level. The pixels of the display are modulated using the density information or values derived from the density representing the corresponding locations. The density information may be overlaid with or combined with ultrasound images, such as B-mode or Doppler images. In alternative or additional embodiments, the density is represented in an image as a value or graph.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for quantifying tissue density using shear wave information in medical ultrasound scanning, the method comprising:
   generating a shear wave in a patient's breast;
   transmitting acoustic energy into the breast while the shear wave propagates within the breast;
   receiving echoes responsive to the transmitting while the shear wave propagates within the breast;
   estimating a shear wave velocity for each of a plurality of locations within the breast as a function of the echoes;
   determining different densities of the breast at the different locations, each of the densities determined as an inverse function of the respective shear wave velocity for the respective location and as a function of a constant for a Young's modulus; and
   outputting an image with pixel locations modulated as a function of the densities at the respective locations.

2. The method of claim 1 wherein generating the shear wave comprises generating the shear wave with focused ultrasound and wherein transmitting and receiving comprises transmitting and receiving repetitively with a same transducer at locations spaced from a focal point of the focused ultrasound.

3. The method of claim 1 wherein estimating comprises estimating the shear wave velocity as a function of spatial displacement caused by the shear wave and a time to peak displacement.

4. The method of claim 1 further comprising:
repeating the determination of the densities at a different time;
calculating a cancer risk as a function of a difference in the densities over time.

5. The method of claim 1 wherein determining the densities comprises linking the shear wave velocity to clinical study data.

6. The method of claim 1 further comprising categorizing the breast as a function of the densities and other information.

7. The method of claim 1 further comprising:
segmenting a lesion as a function of the densities and another tissue characteristic.

8. The method of claim 1 further comprising:
calibrating beamformation as a function of the densities.

9. The method of claim 1 further comprising:
calculating a statistical value for a region including the locations from the densities; and
outputting the statistical value.

* * * * *